US011091412B2

(12) United States Patent
Lu et al.

(10) Patent No.: US 11,091,412 B2
(45) Date of Patent: Aug. 17, 2021

(54) PROCESS FOR PRODUCING ETHYLENE (71) Applicants: China Petroleum & chemical Corporation, Beijing (CN); Shanghai Research Institute of Petrochemical Technology SINOPEC, Shanghai (CN)

(72) Inventors: Hepan Lu, Shanghai (CN); Yangdong Wang, Shanghai (CN); Weisheng Yang, Shanghai (CN); Jiawei Teng, Shanghai (CN)

(73) Assignees: CHINA PETROLEUM & CHEMICAL CORPORATION, Beijing (CN); SHANGHAI RESEARCH INSTITUTE OF PETROCHEMICAL TECHNOLOGY SINOPEC, Shanghai (CN)

( * ) Notice: Subject to any disclaimer, the term of this patent is extended or adjusted under 35 U.S.C. 154(b) by 0 days.

(21) Appl. No.: 16/644,024

(22) PCT Filed: Sep. 3, 2018

(86) PCT No.: PCT/CN2018/103834
§ 371 (c)(1),
(2) Date: Mar. 3, 2020

(87) PCT Pub. No.: WO2019/042449
PCT Pub. Date: Mar. 7, 2019

(65) Prior Publication Data
US 2020/0346996 A1 Nov. 5, 2020

(30) Foreign Application Priority Data

Sep. 4, 2017 (CN) .......................... 201710784627.4
Sep. 4, 2017 (CN) .......................... 201710784654.1

(51) Int. Cl.
*C07C 6/04* (2006.01)
*C10G 11/05* (2006.01)
(Continued)

(52) U.S. Cl.
CPC ................ *C07C 6/04* (2013.01); *C10G 11/05* (2013.01); *C07C 7/04* (2013.01); *C07C 11/04* (2013.01);
(Continued)

(58) Field of Classification Search
CPC .. C07C 6/02; C07C 6/04; C07C 11/04; C07C 7/04; C07C 2521/10; C07C 2523/30; C07C 2529/40; C10G 11/05; Y02P 20/52
See application file for complete search history.

(56) References Cited

U.S. PATENT DOCUMENTS 3,345,285 A    10/1967   Ayres et al.
5,026,935 A *   6/1991   Leyshon ................. C07C 11/04
                                                                                                585/315
(Continued)

FOREIGN PATENT DOCUMENTS

CN        1506343 A    6/2004
CN     207342677 U    5/2018
(Continued)

OTHER PUBLICATIONS

Yoshimura et al. ("Catalytic Cracking of Naphtha to Light Olefins." Catalysis Surveys from Asia vol. 4, p. 157-167, 2001) (Year: 2001).*

*Primary Examiner* — Youngsul Jeong
*Assistant Examiner* — Jason Y Chong
(74) *Attorney, Agent, or Firm* — Novick, Kim & Lee, PLLC; Allen Xue (57) ABSTRACT

A process for producing ethylene includes the steps of: (1) catalytically cracking a raw material hydrocarbon to obtain
(Continued)

a first stream containing propylene; (2) separating the first stream to obtain a C3 component stream; and (3) disproportionating the C3 component stream to obtain an ethylene stream. This process reduces the overall energy consumption of the production process and increases the total yield of the ethylene while obtaining a polymerization-grade ethylene.

26 Claims, 2 Drawing Sheets

(51) Int. Cl.
     *C07C 7/04*      (2006.01)
     *C07C 11/04*     (2006.01)

(52) U.S. Cl.
     CPC ...... *C07C 2521/10* (2013.01); *C07C 2523/30* (2013.01); *C07C 2529/40* (2013.01)

(56) References Cited

U.S. PATENT DOCUMENTS

| | | | | |
|---|---|---|---|---|
| 5,523,502 A | * | 6/1996 | Rubin | C07C 11/04 |
| | | | | 568/697 |
| 2008/0207975 A1 | * | 8/2008 | Crone | C07C 5/3337 |
| | | | | 585/655 |

FOREIGN PATENT DOCUMENTS

| | | |
|---|---|---|
| CN | 207347425 U | 5/2018 |
| CN | 207347428 U | 5/2018 |
| CN | 207347429 U | 5/2018 |
| CN | 207468520 U | 6/2018 |

* cited by examiner

PROCESS FOR PRODUCING ETHYLENE

TECHNICAL FIELD

The invention relates to a process for producing ethylene, in particular to a process for producing polymerization-grade ethylene.

BACKGROUND

The main purpose of industrial steam cracking is to produce low molecular olefins such as ethylene, as well as byproducts of propylene and butadiene, and light aromatics such as benzene, toluene and xylene, and also to generate a small amount of heavy aromatics. Steam cracking is an endothermic reaction, typically carried out in a tubular furnace, in which the raw material and the steam are preheated and entered into the furnace tube, heated to 750-900° C. for cracking, entered into a quenching boiler, cooled rapidly, and then fed into a quencher and a deep-cooling separation device (below −100° C.), to obtain various cracked products in sequence. Steam cracking is the main process for producing low molecular olefins such as ethylene and propylene.

The technology of catalytic cracking an olefin is a process for obtaining light molecular olefins of propylene and ethylene by using various mixed C4-C6 olefin as raw materials and catalytically cracking the olefins contained in the raw materials usually in the presence of a molecular sieve catalyst. Currently, representative olefin catalytic cracking processes mainly comprise: a Propylur process, an OCP process, an Omega process, an OCC process, a Superflex process and the like. Amongst others, the Propylur process results in an olefin conversion up to 85%, a single pass yield of propylene of 40 mol %, a yield of ethylene of 10 mol % (relative to the total amount of olefins in the feed); while the Omega process results in an olefin conversion of more than 75%, and the OCC process results in a single pass conversion of olefins of more than 65%.

SUMMARY OF THE INVENTION

The invention aims to solve the problem of relatively high energy consumption needed by the prior art to carry out cryogenic separation to obtain polymerization-grade ethylene. The present invention thus provides a new process for producing ethylene. Compared with the traditional physical separation method, the process for producing ethylene according to the present invention uses a chemical refining method, which can obtain polymerization-grade ethylene without cryogenic separation.

In the traditional ethylene industry, steam cracking to produce ethylene can simultaneously generate relatively great amounts of by-products of ethane and propane. Methane and ethane need to be separated for obtaining polymerization-grade ethylene, wherein the separation of methane often needs cryogenic separation, and the separation of ethylene from ethane is relatively difficult.

Meanwhile, particularly for a steam cracking device using ethane as a main raw material, because of low yield of propylene, the propylene is often hydrogenated together with the byproduct of C4+ product followed by being recycled to the cracking route. However, the yield of ethylene is not high, generally below 45%, and meanwhile, products from the reaction also need to be subjected to various processes such as demethanization, deethanization and the like.

To solve the above technical problems, the present invention uses the characteristic of a relatively simple separation of a C3 component from a C2 component, thereby converting the olefin-containing species in the raw material into a propylene-containing stream, separating the C3 from C2 in this stream, and then converting the propylene-containing C3 stream back to ethylene through a disproportionation reaction. Because of high selectivity of the disproportionation reaction and thus low amounts of methane and ethane generated, the inventive process can achieve the effect of directly obtaining polymerization-grade ethylene by only controlling the precise separation of C3 from C2 without the need of demethanization under cryogenic separation or deethanization. The process can remarkably save energy required by the whole ethylene production facility, especially the energy required by the separation device. Moreover, the present invention also allows to significantly increase the overall yield of ethylene compared to the traditional route.

According to an embodiment of the present invention, there is provided a process for producing ethylene, comprising the steps of: catalytically cracking a raw material hydrocarbon to obtain a first stream containing propylene; separating the first stream to obtain a C3 component stream; and disproportionating the C3 component stream to obtain an ethylene stream.

In the context of this specification, a C3 component stream is sometimes abbreviated as a C3 component, and an ethylene stream is sometimes abbreviated as ethylene.

According to an embodiment of the present invention, the process for producing ethylene may be carried out according to an embodiment comprising the steps of: feeding a raw material hydrocarbon into an olefin cracking unit for reaction to obtain a C3 component, and feeding all or a part of the C3 component into an olefin disproportionation unit; feeding a propylene-containing stream to the olefin disproportionation unit; and recycling at least a part (all or a part) of the C4+ components generated from the olefin disproportionation unit back to the olefin cracking unit.

According to an embodiment of the present invention, the process for producing ethylene may be carried out according to an embodiment comprising the steps of: feeding a raw material hydrocarbon into an olefin cracking unit for reaction to obtain a C3-containing component, and feeding at least a part of the C3 component into an olefin disproportionation unit; and recycling at least a part (all or a part) of the C4+ components generated from the olefin disproportionation unit back to the olefin cracking unit.

All matters described hereinafter in this specification are equally applicable to the three embodiments, without distinction.

The present invention further relates to one of the following embodiments or any combination thereof.

According to an embodiment of the present invention, there is provided a process for producing ethylene, comprising the steps of:

(1) catalytically cracking a raw material hydrocarbon to obtain a first stream containing propylene, wherein the raw material hydrocarbon comprises at least C4 olefin, preferably at least one olefin selected from the group consisting of C4 olefin, C5 olefin, C6 olefin, C7 olefin and C8 olefin or at least one olefin selected from the group consisting of C4 olefin, C5 olefin and C6 olefin;

(2) separating (e.g., rectifying) the first stream to obtain a C3 component stream; and (3) disproportionating the C3 component stream to obtain an ethylene stream.

The production process according to any one of the preceding or following embodiments, wherein the step (2) comprises the steps of:

(2-1) separating (e.g., rectifying) the first stream to obtain the C3 component stream and a second stream containing ethylene and ethane;

(2-2) optionally, separating the second stream to obtain a ninth stream containing ethylene and a third stream containing ethane; and (2-3) steam cracking all or a part (such as at least 0.1 wt %, at least 50 wt %, or at least 90 wt %) of the third stream to obtain a fourth stream containing ethylene.

The production process according to any one of the preceding or following embodiments, wherein the step (3) comprises the steps of:

(3-1) disproportionating the C3 component stream to obtain an ethylene stream and a fifth stream containing C4 olefin; and (3-2) optionally, recycling at least a part (preferably at least 10 wt %, preferably at least 40 wt %, or preferably at least 60 wt %) of the fifth stream to the step (1).

The production process according to any one of the preceding or following embodiments, wherein in the step (3-1), a sixth stream containing propylene is further obtained, and then at least a part (such as at least 0.1 wt %, at least 50 wt %, or at least 90 wt %) of the sixth stream is recycled to the step (3-1), the step (3) and/or the step (2).

The production process according to any one of the preceding or following embodiments, wherein in the step (1), the reaction conditions for the catalytic cracking comprise: a reaction temperature of 500-600° C. (preferably 540-590° C.), a reaction pressure (gauge pressure) of −0.05 MPa to 0.5 MPa (preferably 0-0.3 MPa), and a volume space velocity of 5-35 $h^{-1}$ (preferably 10-20 $h^{-1}$), in the presence of a molecular sieve (preferably at least one selected from acidic molecular sieves, more preferably at least one selected from the group consisting of silicoaluminophosphate molecular sieves, ZSM molecular sieves and Y molecular sieves, or more preferably ZSM-5 molecular sieves).

The production process according to any one of the preceding or following embodiments, wherein in the step (2) or the step (2-1), the operation conditions for the rectification comprise: an operation temperature of −40° C. to 0° C. (preferably −25° C. to −5° C.), an operation pressure (gauge pressure) of 1.8 MPa to 4.0 MPa (preferably 2.2 MPa to 3.3 MPa), and a theoretical tray number of 10 to 70 (preferably 20 to 50).

The production process according to any one of the preceding or following embodiments, further comprising the steps of:

(4-1) subjecting at least one selected from the group consisting of the ninth stream, the second stream and the fourth stream to a disproportionation reaction with at least one selected from the group consisting of C4 olefin, the raw material hydrocarbon and the fifth stream, to obtain a seventh stream containing propylene;

(4-2) separating the seventh stream, and/or, delivering at least a part (such as at least 0.1 wt %, at least 10 wt %, at least 30 wt %, at least 50 wt %, at least 70 wt %, or at least 90 wt %) of the seventh stream to the step (2), to obtain a C3 component stream; and (4-3) optionally, delivering at least a part (such as at least 50 wt %, at least 70 wt %, or at least 90 wt %) of the C3 component stream to the step (3).

The production process according to any one of the preceding or following embodiments, wherein in the step (3), the C3 component stream is derived in whole or in part from the step (2), or at least a part (such as at least 50 wt %, at least 70 wt %, or at least 90 wt %) of the C3 component stream obtained from the step (2) is fed into the step (3).

The production process according to any one of the preceding or following embodiments, wherein the step (3) comprises the steps of:

(3-I) disproportionating the C3 component stream to obtain a mixture of disproportionation products; and (3-II) separating (e.g. rectifying) the mixture of disproportionation products to obtain an ethylene stream and an eighth stream containing other substances than ethylene, or to obtain an ethylene stream, the fifth stream containing C4 olefin and the sixth stream containing propylene.

The production process according to any one of the preceding or following embodiments, wherein in the step (3-II), the operation conditions for the rectification comprise: an operation temperature of −40° C. to 0° C. (preferably −20° C. to 0° C.), an operation pressure (gauge pressure) of 1.6 MPa to 3.8 MPa (preferably 2.0 MPa to 3.0 MPa), and a theoretical tray number of 5 to 70 (preferably from 20 to 45).

The production process according to any one of the preceding or following embodiments, wherein in the step (3) or in the step (3-1) or in the step (3-I), the reaction conditions for the disproportionation comprise: a reaction temperature of 200-400° C. (preferably 250-350° C.), a reaction pressure (gauge pressure) of 1.0-4.0 MPa (preferably 2.5-3.5 MPa), and a volume space velocity of 0.3-10 $h^{-1}$ (preferably 1-5 $h^{-1}$), in the presence of a metal oxide (such as at least one selected from the group consisting of an oxide of a metal from Group IIA, an oxide of a metal from Group VIB, and an oxide of a metal from Group VIIB, of the periodic table, preferably at least one selected from the group consisting of magnesium oxide, tungsten oxide, molybdenum oxide, and rhenium oxide, more preferably at least one selected from the group consisting of magnesium oxide and tungsten oxide, with or without a carrier therefor).

The production process according to any one of the preceding or following embodiments, wherein the ethylene stream has an ethane content of less than 0.09 vol % (preferably less than 0.04 vol %) and a methane content of less than 100 ppm by vol (preferably less than 10 ppm by vol), relative to the total volume of the ethylene stream.

The production process according to any one of the preceding or following embodiments, wherein the content of propylene in the first stream is at least 40 wt %, preferably at least 70 wt %, relative to the total weight of the first stream.

The production process according to any one of the preceding embodiments, wherein the content of the at least one olefin in the raw material hydrocarbon is at least 30 wt %, preferably at least 50 wt %, relative to the total weight of the raw material hydrocarbon.

Technical Effects

According to the process for producing ethylene of the present invention, in one embodiment, while obtaining polymerization-grade ethylene, the overall energy consumption of the production process, particularly the energy required by the separation device, can be greatly reduced, and the total yield of ethylene can be improved.

According to the process for producing ethylene of the present invention, in one embodiment, cryogenic separation is not used to obtain polymerization-grade ethylene. Accordingly, the low-medium temperature cooling capacity (having a refrigerant temperature <−50° C.) of the process for producing ethylene according to the present invention is 0.

According to the process for producing ethylene of the present invention, in one embodiment, the yield of the polymerization-grade ethylene can be up to 60%.

According to the process for producing ethylene of the present invention, in one embodiment, the overall energy consumption for producing the polymerization-grade ethylene can be reduced by 30% or more as compared with the prior art.

DESCRIPTION OF DRAWINGS

FIG. 1 is a schematic process flow diagram of one embodiment according to the present invention, but the present invention is not limited thereto.
I denotes an olefin cracking unit;
II denotes a C2/C3 separation unit;
V denotes a first olefin disproportionation unit;
0 denotes a raw material hydrocarbon;
1 denotes a first stream;
2 denotes a second stream;
5 denotes a fifth stream;
10 denotes a stream of polymerization-grade ethylene;
11 denotes a C3 component stream;

Stream 0 is fed into unit I to carry out an olefin cracking reaction to generate stream 1, stream 1 is fed into unit II to separate out stream 11, and stream 11 is fed into unit V to obtain stream 10.

FIG. 2 is a schematic process flow diagram of another embodiment of the present invention, but the present invention is not limited thereto.
I denotes an olefin cracking unit;
II denotes a C2/C3 separation unit;
III denotes an ethylene/ethane separation unit;
IV denotes a steam cracking furnace;
V denotes a first olefin disproportionation unit;
0 denotes a raw material hydrocarbon;
1 denotes a first stream;
2 denotes a second stream;
3 denotes a third stream;
4 denotes a fourth stream;
5 denotes a fifth stream;
6 denotes a sixth stream;
8 denotes an eighth stream
9 denotes a ninth stream;
10 denotes stream of polymerization-grade ethylene;
11 denotes a C3 component stream;

Stream 0 is fed into unit I to carry out an olefin cracking reaction to generate stream 1, stream 1 is fed into unit II to be separated into stream 2 and stream 11, stream 2 is fed into unit III to obtain stream 9 and stream 3, stream 3 is fed into unit IV to obtain stream 4, stream 11 is fed into unit V to obtain stream 5, stream 6 and stream 10, a part or all of stream 6 is recycled into unit V, and a part or all of stream 5 is recycled into unit I.

FIG. 3 is a schematic process flow diagram of another embodiment of the present invention, but the present invention is not limited thereto.
I denotes an olefin cracking unit;
II denotes a C2/C3 separation unit;
III denotes an ethylene/ethane separation unit;
IV denotes a steam cracking furnace;
V denotes a first olefin disproportionation unit;
VI denotes a second olefin disproportionation unit;
0 denotes a raw material hydrocarbon;
1 denotes a first stream;
2 denotes a second stream;
3 denotes a third stream;
4 denotes a fourth stream;
5 denotes a fifth stream;
6 denotes a sixth stream;
7 denotes a seventh stream;
8 denotes an eighth stream;
9 denotes a ninth stream;
10 denotes stream of polymerization-grade ethylene;
11 denotes a C3 component stream;

Stream 0 is fed into unit I to carry out an olefin cracking reaction to generate stream 1, stream 1 is fed into unit II to be separated into stream 2 and stream 11, stream 2 is fed into unit III to obtain stream 9 and stream 3, stream 3 is fed into unit IV to obtain stream 4, stream 11 is fed into unit V to obtain stream 5, stream 6 and stream 10, a part or all of stream 6 is recycled to unit V, a part of stream 5 is recycled to unit I, the other part of stream 5 and stream 9 are mixed, the mixture is fed into unit VI to obtain stream 7, and a part or all of stream 7 is recycled to unit II.

FIG. 4 is a schematic process flow diagram of the prior art.
VII denotes a hydrogenation unit;
VIII denotes a steam cracking furnace;
IX denotes an olefin separation unit;
0 denotes a raw material hydrocarbon;
12 denotes stream obtained after hydrogenation;
13 denotes an ethylene-containing stream obtained after steam cracking;
14 denotes stream of polymerization-grade ethylene obtained from the olefin separation unit.

Stream 0 is fed into unit VII to obtain 12, 12 is fed into unit VIII to obtain stream 13, and stream 13 is fed into unit IX to obtain stream 14.

FIG. 5 is a schematic process flow diagram of another prior art.
I denotes a catalytic cracking unit;
IX denotes an olefin separation unit;
0 denotes a raw material hydrocarbon;
15 denotes ethylene obtained after catalytic cracking;
16 denotes a stream of polymerization-grade ethylene obtained from the olefin separation unit.

Stream 0 is fed to unit I to obtain stream 15 and 15 is fed into unit IX to obtain stream 16.

EMBODIMENTS OF THE INVENTION

The embodiments of the present invention are further illustrated in detail below, but it should be noted that the scopes of the present invention are not limited by the embodiments, but are defined by the claims attached.

All publications, patent applications, patents, and other references mentioned in this description are herein incorporated by reference in their entirety. Unless defined otherwise, all technical and scientific terms used herein have the same meaning as commonly understood by those skilled in the art. In case of conflict, definitions provided by the present description will control.

When the description uses terms "known to those skilled in the art", "prior art", or the like, to modify materials, substances, methods, procedures, devices, or components, etc., it is intended that the subject matter modified by the terms encompasses those conventionally used in the art at the time of filing this application, but also encompasses those that are not currently in use, but would become known in the art to be suitable for similar purposes.

In the context of the present invention, the term "C3 component" refers to propylene or a hydrocarbon mixture having propylene as the major component. For example, the propylene content in the hydrocarbon mixture is generally 30 wt % or more, preferably 60 wt % or more.

In the context of the present invention, the term "C4 olefin" refers to a mono-olefin having four carbon atoms. For example, as C4 olefin, various isomers of butene such as 1-n-butene, 2-n-butene, and isobutene are encompassed. In addition, the term "C4+ olefin" refers to a mono-olefin having more than four carbon atoms or a mixture thereof in any proportion. Other similar expressions, such as C5 olefin, and the like are also similarly understood.

In the context of the present invention, the term "C4+ component" refers to a C4+ olefin or a hydrocarbon mixture having C4+ olefins as the major component. For example, the weight content of C4+ olefins in the hydrocarbon mixture is generally 40 wt % or more, preferably 80 wt % or more.

In the context of the present invention, the term "polymerization-grade ethylene" refers to ethylene satisfying the requirements on purity of the feed of a polymerization. For example, polymerization-grade ethylene typically has an ethylene purity of greater than 99.9%, preferably greater than 99.95%. More specifically, for example, the polymerization-grade ethylene generally has an ethane content of less than 0.09 vol %, preferably less than 0.04 vol %, and a methane content of generally less than 100 ppm by volume, preferably less than 10 ppm by volume, relative to the total volume of the polymerization-grade ethylene.

In the context of the present invention, the olefin separation unit IX refers to a process using conventional methods to separate ethylene-containing gas, such as steam cracked gas, catalytically cracked gas, etc., which typically involves demethanization or dehydrogenation at a low temperature.

Without otherwise specifically indicated, all percentages, parts, ratios, etc. mentioned in this description are provided by weight, unless the basis by weight does not conform to the conventional knowledge of those skilled in the art.

In the context of this description, any two or more aspects or embodiments of the present invention may be combined arbitrarily, and the thus resulted embodiments are parts of the original disclosure of the present description, and also fall within the protection scopes of the present invention.

The present invention relates to a process for producing ethylene, and more particularly to a process for producing polymerization-grade ethylene. Compared with the prior art, the process can greatly reduce the overall energy consumption of the production process (especially the energy requirement by the separation device), and can also produce non-polymerization-grade ethylene as required, thereby improving the total yield of ethylene.

According to an embodiment of the present invention, the process for producing ethylene comprises the steps of:
(1) catalytically cracking a raw material hydrocarbon to obtain a first stream containing propylene;
(2) separating the first stream to obtain a C3 component stream; and
(3) disproportionating the C3 component stream to obtain an ethylene stream.

According to an embodiment of the present invention, in the process for producing ethylene or in the step (1), the raw material hydrocarbon contains at least a C4 olefin, preferably at least one olefin selected from the group consisting of C4 olefin, C5 olefin, C6 olefin, C7 olefin and C8 olefin, or at least one olefin selected from the group consisting of C4 olefin, C5 olefin and C6 olefin.

According to an embodiment of the present invention, in the process for producing ethylene or in the step (1), the content of the olefin or of the at least one olefin in the raw material hydrocarbon is not particularly limited, but by way of example, the content of the olefin or of the at least one olefin in the raw material hydrocarbon is generally at least 30 wt %, preferably at least 50 wt %, relative to the total weight of the raw material hydrocarbon.

According to an embodiment of the present invention, in the step (1), the content of propylene in the first stream is generally at least 40 wt %, preferably at least 70 wt %, relative to the total weight of the first stream.

According to an embodiment of the present invention, in the step (1), the catalytic cracking may be carried out in any manner and any method conventionally known in the art, as long as the raw material hydrocarbon can be converted into propylene, without any particular limitation.

According to an embodiment of the invention, the catalytic cracking may be carried out in the presence of a molecular sieve. As the molecular sieve, any type used in the art for this purpose can be used, and specifically, for example, acidic molecular sieves, more specifically, silicoaluminophosphate molecular sieves, ZSM molecular sieves, and Y molecular sieves, particularly SAPO-34 or ZSM-5 molecular sieves, can be used. These molecular sieves may be used alone or as a combination in any ratio. Further, such molecular sieves can be commercially available as they are, or can be produced by any method known in the art, for which the present invention does not provide any particular limitation thereto.

According to an embodiment of the present invention, in the step (1), the reaction temperature for the catalytic cracking is not particularly limited, which is however generally 500-600° C., preferably 540-590° C.

According to an embodiment of the present invention, in the step (1), the reaction pressure (gauge pressure) for the catalytic cracking is not particularly limited, which is however generally −0.05 MPa to 0.5 MPa, preferably 0-0.3 MPa.

According to an embodiment of the present invention, in the step (1), the volume space velocity for the catalytic cracking is not particularly limited, which is however generally 5 to 35 $h^{-1}$, preferably 10 to 20 $h^{-1}$.

According to an embodiment of the present invention, in the process for producing ethylene, the step (2) may optionally comprise step (2-1), or may further optionally comprise step (2-2) and step (2-3).

Step (2-1) separates the first stream to obtain the C3 component stream and a second stream containing ethylene and ethane.

According to an embodiment of the present invention, in the step (2), the separation may be, for example, rectification or fractionation, particularly rectification. The separation or the rectification or fractionation may be carried out in any manner and any method conventionally known in the art, as long as the C3 component can be effectively separated from the first stream, without any particular limitation.

According to an embodiment of the present invention, in the step (2-1), the separation may be, for example, rectification or fractionation, particularly rectification. The separation or the rectification or fractionation may be carried out in any manner and any method conventionally known in the art, as long as an effective separation of the C3 component from ethylene and ethane is achieved, thereby obtaining the C3 component stream and the second stream containing ethylene and ethane, without particular limitation.

According to an embodiment of the present invention, in the step (2) or in the step (2-1), the operation temperature for the rectification is not particularly limited, which is however generally −40° C. to 0° C., preferably −25° C. to −5° C. The operation pressure (gauge pressure) for the rectification is not particularly limited, which is however generally 1.8 to 4.0 MPa, preferably 2.2 to 3.3 MPa. Also, the theoretical tray number for the rectification is not particularly limited, which is however generally 10 to 70, preferably 20 to 50.

Step (2-2) separates the second stream to obtain a ninth stream containing ethylene and a third stream containing ethane.

According to an embodiment of the present invention, in the step (2-2), as the separation, for example, distillation or fractionation, or even a cryogenic separation, may be mentioned. The separation may be carried out in any manner and by any method conventionally known in the art, as long as an effective separation of ethylene and ethane can be achieved, thereby obtaining the ninth stream containing ethylene and the third stream containing ethane, without particular limitation. The person skilled in the art can directly refer to the relevant knowledge known in the art, and the description does not repeat here.

Step (2-3) steam cracks all or at least 0.1 wt %, at least 50 wt %, or at least 90 wt % of the third stream to obtain a fourth stream containing ethylene.

According to an embodiment of the present invention, in the step (2-3), the steam cracking may be carried out in any manner and any method conventionally known in the art, as long as all or a part of the hydrocarbons (such as ethane) contained in the third stream can be effectively cracked into ethylene, without particular limitation. The person skilled in the art can directly refer to the relevant knowledge known in the art, and the description does not repeat here.

According to an embodiment of the present invention, in the step (3), the disproportionation may be carried out in any manner and any method conventionally known in the art, as long as the C3 component can be effectively converted into ethylene, without any particular limitation.

According to an embodiment of the present invention, in the step (3), for example, the disproportionation reaction may be generally carried out in the presence of a metal oxide (as a catalyst). Examples of the metal oxide comprise an oxide of a metal from Group IIA of the periodic table, an oxide of a metal from Group VIB of the periodic table, and an oxide of a metal from Group VIIB of the periodic table of the periodic table, and more specifically, magnesium oxide, tungsten oxide, molybdenum oxide, and rhenium oxide, and particularly, magnesium oxide and tungsten oxide. In addition, the metal oxide may be of a bulk type (no carrier is present) or a supported type. Examples of the carrier for the supported metal oxide comprise refractory metal oxides, and more specifically, silica, alumina, zirconia, and the like. These disproportionation catalysts may be used alone or as a combination in an arbitrary ratio. Further, such disproportionation catalysts are commercially available as they are, or may be produced by any method known in the art, for which the present invention does not provide any particular limitation thereto.

According to an embodiment of the present invention, in the step (3), the reaction temperature for the disproportionation reaction is not particularly limited, which is however generally 200-400° C., preferably 250-350° C.

According to an embodiment of the present invention, in the step (3), the reaction pressure (gauge pressure) for the disproportionation reaction is not particularly limited, which is however generally 1.0 to 4.0 MPa, preferably 2.5 to 3.5 MPa.

According to an embodiment of the present invention, in the step (3), the volume space velocity for the disproportionation reaction is not particularly limited, which is however generally 0.3 to 10 $h^{-1}$, preferably 1 to 5 $h^{-1}$.

According to an embodiment of the present invention, in the step (3), the ethylene stream obtained is a polymerization-grade ethylene stream, or the ethylene stream is subjected to a simple purification treatment (such as distillation) for the light and heavy components, so as to form a polymerization-grade ethylene stream.

According to an embodiment of the invention, in the step (3), the C3 component stream is derived in whole or in part from the step (2). In other words, as needed, it is allowed that only a part of the C3 component stream to be treated in the step (3) is derived from the step (2), while the remaining part of the stream (sometimes called as a stream containing propylene) may be derived from other sources, such as a C3 component produced by other production devices, or even may be an outsourced C3 component, without any particular limitation.

According to an embodiment of the present invention, at least a part of the C3 component stream obtained from the step (2) is sent to the step (3). For example, all or at least 50 wt %, at least 70 wt %, or at least 90 wt % of the C3 component stream obtained from the step (2) is sent to the step (3).

According to an embodiment of the present invention, in the process for producing ethylene, the step (3) may comprise the step (3-1), or may further optionally comprise the step (3-2).

Step (3-1) disproportionates the C3 component stream to obtain an ethylene stream and a fifth stream containing C4 olefin.

According to an embodiment of the present invention, in the step (3-1), the disproportionation may be carried out in any manner and any method conventionally known in the art, as long as the C3 component can be effectively converted into ethylene and C4 olefin, without particular limitation.

According to an embodiment of the present invention, in the step (3-1), for example, the disproportionation reaction may be generally carried out in the presence of a metal oxide (as a catalyst). Examples of the metal oxide comprise an oxide of a metal from Group IIA of the periodic table, an oxide of a metal from Group VIB of the periodic table, and an oxide of a metal from Group VIIB of the periodic table of the periodic table, more specifically, magnesium oxide, tungsten oxide, molybdenum oxide, and rhenium oxide, and particularly, magnesium oxide and tungsten oxide. In addition, the metal oxide may be of a bulk type (no carrier is present) or a supported type. Examples of the carrier for the supported metal oxide comprise refractory metal oxides, and more specifically, silica, alumina, zirconia, and the like. These disproportionation catalysts may be used alone or as a combination in an arbitrary ratio. Further, such disproportionation catalysts are commercially available as they are, or may be produced by any method known in the art, for which the present invention does not provide any particular limitation thereto.

According to an embodiment of the present invention, in the step (3-1), the reaction temperature for the disproportionation reaction is not particularly limited, which is however generally 200-400° C., preferably 250-350° C.

According to an embodiment of the present invention, in the step (3-1), the reaction pressure (gauge pressure) for the disproportionation reaction is not particularly limited, which is however generally 1.0 to 4.0 MPa, preferably 2.5 to 3.5 MPa.

According to an embodiment of the present invention, in the step (3-1), the volume space velocity for the disproportionation reaction is not particularly limited, which is however generally 0.3 to 10 $h^{-1}$, preferably 1 to 5 $h^{-1}$.

According to an embodiment of the present invention, in the step (3-1), the ethylene stream obtained is itself a polymerization-grade ethylene stream, or the ethylene stream is subjected to a simple purification treatment (such as distillation) for the light and heavy components, so as to form a polymerization-grade ethylene stream.

According to an embodiment of the present invention, in the step (3-1), the C3 component stream may be directly separated into the ethylene stream and the fifth stream containing C4 olefin after disproportionation. Additionally, as the fifth stream typically contains higher olefins in addition to the C4 olefin, the fifth stream is sometimes called as a C4+ component stream.

Step (3-2) recycles all or at least 40 wt %, at least 70 wt %, or at least 90 wt % of the fifth stream to the step (1).

According to an embodiment of the present invention, as the disproportionation reaction is an equilibrium reaction, the product mixture from the disproportionation contains not only ethylene and C4 olefin, but also typically the unreacted raw material, i.e., propylene or C3 component. Accordingly, in the step (3-1), in addition to the ethylene stream and the fifth stream containing C4 olefin, a sixth stream containing propylene (unreacted C3 component) is generally obtained.

According to an embodiment of the invention, all or at least 0.1 wt %, at least 50 wt %, or at least 90 wt % of the sixth stream is recycled to the step (3-1), to the step (3), to the step (2), or to at least two of these steps.

According to an embodiment of the present invention, in the process for producing ethylene, the step (3) may be carried out, for example, in the manner according to the steps (3-I) and (3-II).

Step (3-I) disproportionates the C3 component stream to obtain a mixture of disproportionation products.

According to an embodiment of the present invention, in the step (3-I), the disproportionation may be carried out in the same manner as the step (3), which will not be repeated herein.

Step (3-II) separates the mixture of disproportionation products to obtain an ethylene stream and an eighth stream containing other substances than ethylene, or to obtain an ethylene stream, the fifth stream containing C4 olefin, and the sixth stream containing propylene.

According to an embodiment of the present invention, in the step (3-II), the separation may be, for example, rectification or fractionation, particularly rectification. The separation, or the rectification or fractionation, may be carried out in any manner and any method conventionally known in the art, as long as the mixture of disproportionation products can be effectively separated into the respective streams, without any particular limitation. Nonetheless, for example, the present invention does not particularly limit the operation temperature for the distillation, which is however generally −40° C. to 0° C., preferably −20° C. to 0° C. The operation pressure (gauge pressure) for the rectification is not particularly limited, which is however generally 1.6 to 3.8 MPa, preferably 2.0 to 3.0 MPa. The theoretical tray number for the rectification is not particularly limited, which is however generally 5 to 70, preferably 20 to 45.

According to an embodiment of the present invention, in the step (3-II), the ethylene stream obtained is itself a polymerization-grade ethylene stream, or the ethylene stream is subjected to a simple purification treatment (such as distillation) for the light and heavy component, so as to form a polymerization-grade ethylene stream.

According to an embodiment of the present invention, the process for producing ethylene may further comprise the following step (4-1) and step (4-2), and may further comprise an optional step (4-3) as needed.

Step (4-1) subjects at least one selected from the group consisting of the ninth stream, the second stream and the fourth stream to a disproportionation reaction with at least one selected from the group consisting of the C4 olefin, the raw material hydrocarbon and the fifth stream, to obtain a seventh stream containing propylene. Here, the C4 olefin is not the C4 olefin generated from the process for producing ethylene according to the present invention, but is, for example, a C4 olefin that may be provided by other plants or production processes, or be outsourced. In addition, the disproportionation may be carried out in the exactly same manner as in the step (3), which will not be repeated here again.

Step (4-2) separates the seventh stream and/or, delivers at least a part of the seventh stream to the step (2), to obtain a C3 component stream.

According to an embodiment of the present invention, in the step (4-2), the separation may be carried out in the same manner as in the step (2) or the step (2-1), which will not be repeated here again.

According to an embodiment of the invention, for example, at least 0.1 wt %, at least 10 wt %, at least 30 wt %, at least 50 wt %, at least 70 wt %, or at least 90 wt %, of the seventh stream is delivered to the step (2).

Step (4-3) delivers all or at least 50 wt %, at least 70 wt %, or at least 90 wt %, of the C3 component stream to the step (3).

EXAMPLES

The present invention will be described in further detail with reference to the Examples below, whilst the present invention is not limited to these Examples.

In the context of the present specification, including in the following Examples and Comparative Examples, the overall yield of ethylene is defined as: ethylene weight flow rate in all ethylene-containing streams of the present invention/total weight flow rate of the raw materials; and the overall yield of polymerization-grade ethylene is defined as: the weight flow rate of the polymerization-grade ethylene directly obtained by the invention/the total weight flow rate of the raw materials. In the present invention, there are some streams containing ethylene, such as ethylene-containing streams obtained by catalytic cracking or steam cracking, which streams contribute to the yield of ethylene, but which are not of the polymerization-grade in morphology, so that in the Examples, the overall yield of ethylene is greater than the yield of polymerization-grade ethylene.

In the context of this specification, including the following Examples and Comparative Examples, the overall energy consumption is calculated according to GB/T50441-2016, which calculates the energy consumptions of various public works within the boundaries, including but not limited to: steam, circulating water, electricity, refrigerant, fuel gas, and the like.

In the context of this specification, including the Examples and Comparative Examples below, all reagents and materials are either commercially available or can be prepared according to known knowledge.

In the following Examples and Comparative Examples, % represents wt %, space velocity represents weight space velocity, and pressure represents gauge pressure.

Example 1

Figure 1:
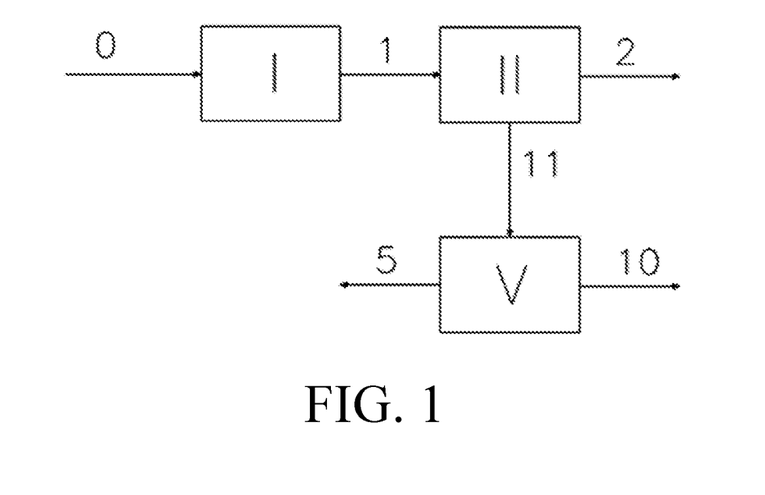

The flow chart shown in FIG. 1 was adopted:
Stream 0 contained 50% C4 olefin, 20% C5 olefin, 15% C6 olefin, 5% C7 olefin, 5% C8 olefin, and 5% C4 alkane, with a total flow rate of 1000 kg/h. Stream 0 was fed into unit I for reaction, wherein the unit I utilized the OCC technology from Shanghai Petrochemical Research Institute, and the catalyst was an OCC-II type catalyst, with a reaction temperature of 590° C., a reaction pressure of 0.01 MPa, and a reaction space velocity of 20 $h^{-1}$. Stream 0 was subjected to catalytic cracking reaction in the unit I to obtain stream 1 containing ethylene and propylene. Stream 1 was fed into unit II, wherein the unit II utilized a common rectification method, with a column pressure of 2.4 MPa, a column top temperature of −24° C., a theoretical tray number of 50, so as to obtain a C3 stream 11 with a C2 content of less than 0.09% at the column bottom, and stream 2 with an ethylene content of 70% at the column top. Stream 11 was fed into unit V, wherein the unit utilized an OMT-R technology from Shanghai Petrochemical Research Institute, and the catalyst was an OMT-II type, with a reaction temperature of 250° C., a reaction pressure of 2.6 MPa, and a reaction space velocity of 1 $h^{-1}$. After propylene being disproportionated into ethylene and C4 olefin in the unit, rectification for separation was carried out to provide stream 10 and stream 5 under the conditions of a column pressure of 2.1 MPa, a column top temperature of −15° C., and a theoretical tray number of 45.

The ethylene purity in stream 10 was >99.9% at a flow rate of 120 kg/h, the ethylene purity in stream 2 was 70% at a flow rate of 168 kg/h, and the total ethylene output was 288 kg/h.

The overall ethylene yield was 28.8%, with a polymerization-grade ethylene yield of 12%, and an overall energy consumption of 150 kg EO/t feed, 536 kg EO/t ethylene, and 1250 kg EO/t polymerization-grade ethylene.

Example 2

Figure 2:
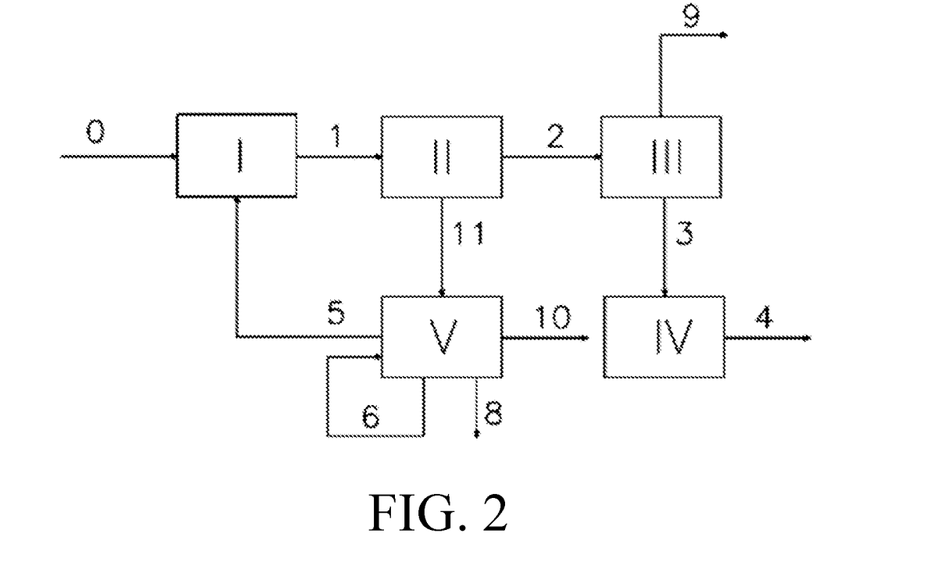
Figure 3:
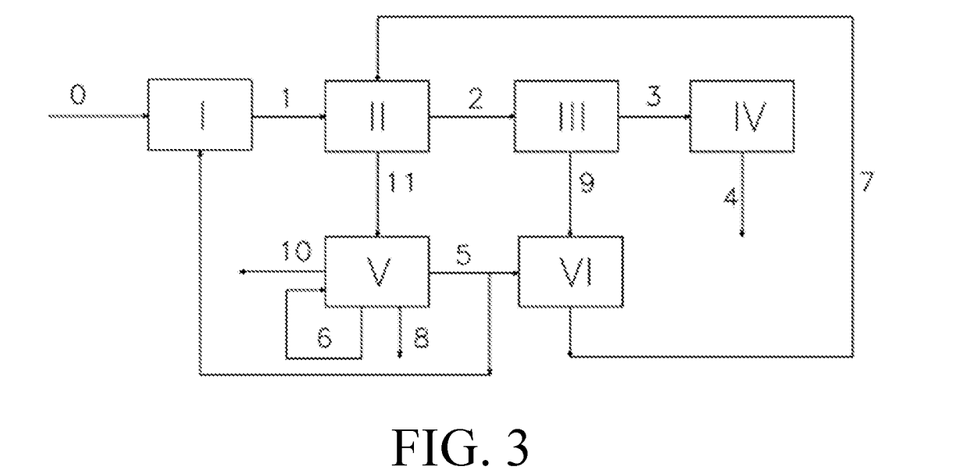

The flow chart shown in FIG. 2 was adopted:
Stream 0 contained 50% C4 olefin, 20% C5 olefin, 15% C6 olefin, 5% C7 olefin, 5% C8 olefin, and 5% C4 alkane, with a total flow rate of 1000 kg/h. Stream 0 was fed into unit I for reaction, wherein the unit I utilized the OCC technology from Shanghai Petrochemical Research Institute, and the catalyst was an OCC-II type catalyst, with a reaction temperature of 590° C., a reaction pressure of 0.011 MPa, and a reaction space velocity of 20 $h^{-1}$. Stream 0 was subjected to catalytic cracking reaction in the unit I to obtain stream 1 containing ethylene and propylene. Stream 1 was fed into unit II, wherein the unit II utilized a common rectification method, with a column pressure of 2.4 MPa, a column top temperature of −24° C., and a theoretical tray number of 50, so as to obtain stream 2 with an ethylene content of 70% at the column top, and a C3 stream 11 with a C2 content of less than 0.09% at the column bottom. Stream 2 was fed into unit III, wherein the unit III utilized a common rectification method, with a column pressure of 3.0 MPa, a column top temperature of −28° C., and a number of theoretical tray number of 70. Stream 9 and stream 3 were obtained from the unit III, which streams were fed into unit IV to obtain stream 4. Stream 11 was fed into unit V, wherein the unit utilized an OMT-R technology from Shanghai Petrochemical Research Institute, and the catalyst was OMT-II type, with a reaction temperature of 250° C., a reaction pressure of 2.6 MPa, and a reaction space velocity of 1 $h^{-1}$. After propylene being disproportionated into ethylene and C4 olefin in the unit, rectification for separation was carried out to provide stream 10 and stream 5 under the conditions of a column pressure of 2.1 MPa, a column top temperature of −15° C., and a theoretical tray number of 45. Stream 5 was recycled in its entirety to unit I.

The ethylene-containing streams were streams 10, 9, and 4, wherein the ethylene purity in stream 10 was >99.9% at a flow rate of 310 kg/h; the purity of the ethylene in stream 9 was 88% at a flow rate of 300 kg/h; and the ethylene flow rate of stream 4 was 15 kg/h. The total output of ethylene was 625 kg/h.

The total yield of ethylene was 62.5%, wherein the yield of polymerization-grade ethylene was 31%, and the overall energy consumption was as follows: 230 kg EO/t feed, 368 kgEO/t ethylene, and 742 kgEO/t polymerization-grade ethylene.

Example 3

The flow chart shown in FIG. 2 was adopted:
Stream 0 contained 50% C4 olefin, 20% C5 olefin, 15% C6 olefin, 5% C7 olefin, 5% C8 olefin, and 5% C4 alkane, with a total flow rate of 1000 kg/h. Stream 0 was fed into unit I for reaction, wherein the unit I utilized the OCC technology from Shanghai Petrochemical Research Institute, and the catalyst was an OCC-II type catalyst, with a reaction temperature of 590° C., a reaction pressure of 0.011 MPa, and a reaction space velocity of 20 $h^{-1}$. Stream 0 was subjected to catalytic cracking reaction in the unit I to obtain stream 1 containing ethylene and propylene. Stream 1 was fed into unit II, wherein the unit II utilized a common rectification method, with a column pressure of 2.4 MPa, a column top temperature of −24° C., and a theoretical tray number of 50, so as to obtain stream 2 with an ethylene content of 70% at the column top, and a C3 stream 11 with a C2 content of less than 0.09% at the column bottom. Stream 2 was fed into unit III, wherein the unit III utilized a common rectification method, with a column pressure of 3.5 MPa, a column top temperature of −30° C., and a number of theoretical tray number of 70. Stream 9 and stream 3 were obtained from the unit III, which streams were fed into unit IV to obtain stream 4. Stream 11 was fed into unit V, wherein the unit utilized an OMT-R technology from Shanghai Petrochemical Research Institute, and the catalyst was of an OMT-II type, with a reaction temperature of 250° C., a reaction pressure of 2.6 MPa, and a reaction space velocity of 1 $h^{-1}$. After propylene being disproportionated into ethylene and C4 olefin in the unit, rectification for separation was carried out to provide stream 10 and stream 5 under the conditions of a column pressure of 2.1 MPa, a column top temperature of −15° C., and a theoretical tray number of 45. 60% of stream 5 was recycled to unit I. The rest of 40% of stream 5 was mixed with stream 9, and then fed into unit VI to obtain stream 7, wherein the unit VI utilized the OMT technology from Shanghai Petrochemical Research Institute, and the catalyst was an OMT-I type, with a reaction temperature of 260° C., a reaction pressure of 2.8 MPa, and a reaction space velocity of 1.5 $h^{-1}$, and stream 7 passed through the unit VI was completely recycled to unit II.

The ethylene-containing streams were streams 10 and 4, where the ethylene purity in stream 10 was >99.9% at a flow rate of 560 kg/h; and the ethylene flow rate of stream 4 was 25 kg/h. The total output of ethylene was 585 kg/h.

The total yield of ethylene was 58.5%, wherein the yield of polymerization-grade ethylene was 56%, and the overall energy consumption was as follows: 255 kgEO/t feed, 436 kgEO/t ethylene, and 455 kgEO/t polymerization-grade ethylene.

Comparative Example 1

Figure 4:
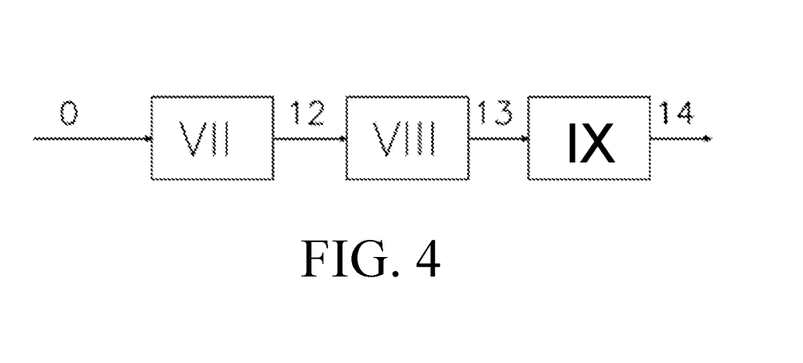

The flow chart shown in FIG. 4 was adopted:

Stream 0 contained 50% C4 olefin, 20% C5 olefin, 15% C6 olefin, 5% C7 olefin, 5% C8 olefin, and 5% C4 alkane, with a total flow rate of 1000 kg/h.

Stream 0 was fed into unit VII to obtain stream 12, stream 12 was fed into unit VIII to obtain stream 13, and stream 13 was fed into unit IX to obtain stream 14.

The ethylene-containing stream was stream 14, wherein the ethylene purity was >99.9% at a flow rate of 300 kg/h; and the total output of ethylene was 300 kg/h.

The total yield of ethylene was 30%, wherein the yield of polymerization-grade ethylene was 30%, and the overall energy consumption was as follows: 216 kgEO/t raw material, 720 kgEO/t ethylene, and 720 kgEO/t polymerization-grade ethylene.

Comparative Example 2

Figure 5:
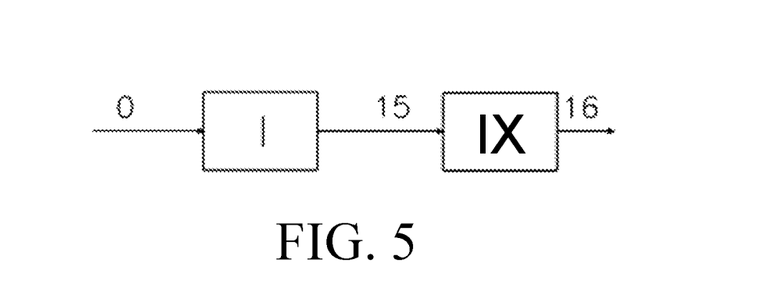

The flow chart shown in FIG. 5 was adopted:

Stream 0 contained 50% C4 olefin, 20% C5 olefin, 15% C6 olefin, 5% C7 olefin, 5% C8 olefin, and 5% C4 alkane, with a total flow rate of 1000 kg/h.

Stream 0 was fed into unit I to obtain stream 15, and stream 15 was fed into unit IX to obtain stream 16.

The ethylene-containing stream was stream 16, wherein the ethylene purity was >99.9% at a flow rate of 178 kg/h; and the total output of ethylene was 178 kg/h.

The total yield of ethylene was 17.8%, wherein the yield of polymerization-grade ethylene was 17.8%, and the overall energy consumption was as follows: 249 kgEO/t feed, 1494 kgEO/t ethylene, and 1494 kgEO/t polymerization-grade ethylene.

TABLE 1

| Examples | Total yield of ethylene % | Yield of polymerization-grade ethylene % | Energy consumption/t raw material, kg EO | Energy consumption/t ethylene, kg EO | Energy consumption/t Polymerization-grade ethylene, kg EO |
|---|---|---|---|---|---|
| Example 1 | 28.8 | 12 | 150 | 536 | 1250 |
| Example 2 | 62.5 | 31 | 230 | 368 | 742 |
| Example 3 | 58.5 | 56 | 255 | 436 | 455 |
| Comparative Example 1 | 30 | 30 | 216 | 720 | 720 |
| Comparative Example 2 | 17.8 | 17.8 | 249 | 1399 | 1399 |

The invention claimed is:

1. A process for producing ethylene, comprising the steps of:
   (1) catalytically cracking a raw material hydrocarbon to obtain a first stream containing propylene, wherein the raw material hydrocarbon comprises at least C4 olefin;
   (2) separating the first stream to obtain a C3 component stream,
   wherein the step (2) comprises:
   (2-1) separating the first stream to obtain the C3 component stream and a second stream containing ethylene and ethane;
   (3) disproportionating at least a part of the C3 component stream to obtain an ethylene stream,
   wherein the step (3) comprises:
   (3-1) disproportionating at least a part of the C3 component stream to obtain the ethylene stream and a fifth stream containing C4 olefin; and
   (3-2) recycling at least a part of the fifth stream to the step (1); and
   (4) disproportionating at least a part of the second stream to obtain a seventh stream containing propylene,
   wherein the step (4) comprises:
   (4-1) subjecting a part of the second stream to a disproportionation reaction with at least one selected from the group consisting of an externally obtained stream comprising C4 olefin, a part of the raw material hydrocarbon, and a part of the fifth stream to obtain the seventh stream containing propylene; and
   (4-2) separating the seventh stream and/or delivering at least a part of the seventh stream to the step (2) to obtain the C3 component stream.

2. The process according to claim 1, wherein the step (2) further comprises:
   (2-2) separating a part of the second stream to obtain a ninth stream containing ethylene and a third stream containing ethane; and
   (2-3) steam cracking all or a part of the third stream to obtain a fourth stream containing ethylene.

3. The process according to claim 2, wherein at least 90 wt % of the third stream is subject to steam cracking in the step (2-3).

4. The process according to claim 1, wherein, in step (3-2), at least 60 wt % of the fifth stream is recycled to the step (1).

5. The process according to claim 1, where in the step (3-1), a sixth stream containing propylene is further obtained, and then at least a part of the sixth stream is recycled to the step (3-1), to the step (3) and/or to the step (2).

6. The process according to claim 5, wherein, in the step (3-1), at least 90 wt % of the sixth stream is recycled to the step (3-1), to the step (3) and/or to the step (2).

7. The process according to claim 1, wherein, in the step (1), the reaction conditions for the catalytic cracking comprise: a reaction temperature of 500-600° C., a reaction pressure (gauge pressure) of −0.05 MPa to 0.5 MPa, and a volume space velocity of 5-35h$^{-1}$, in the presence of a molecular sieve.

8. The process according to claim 7, wherein the reaction conditions for the catalytic cracking comprise: a reaction temperature of 540-590° C., a reaction pressure (gauge pressure) of 0-0.3 MPa, and a volume space velocity of 10-20h$^{-1}$, in the presence of ZSM-5 molecular sieves.

9. The process according to claim 1, wherein in the step (2) or in the step (2-1), separating is rectifying and the operation conditions for the rectification comprise: an operation temperature of −40° C. to 0° C., an operation pressure (gauge pressure) of 1.8 MPa to 4.0 MPa, and a theoretical tray number of 10 to 70.

10. The process according to claim 9, wherein the operation conditions for the rectification comprise: an operation temperature of −25° C. to −5° C., an operation pressure (gauge pressure) of 2.2 MPa to 3.3 MPa, and a theoretical tray number of 20 to 50.

11. The process according to claim 1, wherein the step (3-1) comprises:
(3-1-1) disproportionating the C3 component stream to obtain a mixture of disproportionation products; and
(3-1-11) separating the mixture of the disproportionation products to obtain the ethylene stream, the fifth stream containing C4 olefin and an eighth stream containing other substances than ethylene, or to obtain the ethylene stream, the fifth stream containing C4 olefin and a sixth stream containing propylene.

12. The process according to claim 11, wherein in the step (3-II), separating is rectifying, and the operation conditions for the rectification comprise: an operation temperature of −40° C. to 0° C., an operation pressure (gauge pressure) of 1.6 MPa to 3.8 MPa, and a theoretical tray number of 5 to 70.

13. The process according to claim 12, wherein the operation conditions for the rectification comprise: an operation temperature of −20° C. to 0° C., an operation pressure (gauge pressure) of 2.0 MPa to 3.0 MPa, and a theoretical tray number of 20 to 45.

14. The process according to claim 1, wherein in the step (3), the reaction conditions for the disproportionation comprise: a reaction temperature of 200-400° C., a reaction pressure (gauge pressure) of 1.0-4.0 MPa, and a volume space velocity of 0.3-10h$^{-1}$, in the presence of a metal oxide.

15. The process according to claim 14, wherein in the step (3), the reaction conditions for the disproportionation comprise: a reaction temperature of 250-350° C., a reaction pressure (gauge pressure) of 2.5-3.5 MPa, and a volume space velocity of 1-5h$^{-1}$, in the presence of at least one selected from magnesium oxide and tungsten oxide, with or without a carrier therefor.

16. The process according to claim 1, wherein the ethylene stream has an ethane content of less than 0.09 vol % and a methane content of less than 100 ppm by volume, relative to the total volume of the ethylene stream.

17. The process according to claim 16, wherein the ethylene stream has an ethane content of less than 0.04 vol % and a methane content of less than 10 ppm by volume, relative to the total volume of the ethylene stream.

18. The process according to claim 1, wherein the content of propylene in the first stream is at least 70 wt %, relative to the total weight of the first stream.

19. The process according to claim 1, wherein the content of olefins in the raw material hydrocarbon is at least 30 wt %, relative to the total weight of the raw material hydrocarbon.

20. The process according to claim 19, wherein the content of olefins in the raw material hydrocarbon is at least 50 wt %, relative to the total weight of the raw material hydrocarbon.

21. The process according to claim 1, wherein the raw material hydrocarbon additionally comprises at least one olefin selected from the group consisting of C5 olefin, C6 olefin, C7 olefin, and C8 olefin.

22. The process according to claim 1, wherein, in the step (4-2), delivering at least 10 wt % of the seventh stream to the step (2) to obtain the C3 component stream.

23. The process according to claim 1, wherein, in the step (4-2), delivering at least 50 wt % of the seventh stream to the step (2) to obtain the C3 component stream; and/or, delivering at least 50 wt % of the C3 component stream to the step (3).

24. The process according to claim 1, wherein, in the step (4-2), delivering at least 90 wt % of the seventh stream to the step (2) to obtain the C3 component stream; and/or, delivering at least 90 wt % of the C3 component stream to the step (3).

25. The process according to claim 1, wherein at least 90 wt % of the C3 component stream obtained in the step (2) is delivered to the step (3).

26. A process for producing ethylene, comprising the steps of:
(1) catalytically cracking a raw material hydrocarbon to obtain a first stream containing propylene, wherein the raw material hydrocarbon comprises at least C4 olefin;
(2) separating the first stream to obtain a C3 component stream,
wherein the step (2) comprises:
(2-1) separating the first stream to obtain the C3 component stream and a second stream containing ethylene and ethane;
(2-2) separating the second stream to obtain a ninth stream containing ethylene and a third stream containing ethane; and
(2-3) steam cracking all or a part of the third stream to obtain a fourth stream containing ethylene;
(3) disproportionating at least a part of the C3 component stream to obtain an ethylene stream,
wherein the step (3) comprises:
(3-1) disproportionating at least a part of the C3 component stream to obtain the ethylene stream and a fifth stream containing C4 olefin; and
(3-2) recycling at least a part of the fifth stream to the step (1);
(4) disproportionating at least a part of the ninth stream, a part of the second stream, and a part of the fourth stream to obtain a seventh stream containing propylene,
wherein the step (4) comprises:
(4-1) subjecting at least one selected from a part of the ninth stream, a part of the second stream, and a part of the fourth stream to a disproportionation reaction with at least one selected from the group consisting of an externally obtained stream comprising C4 olefin, a part of the raw material hydrocarbon, and a part of the fifth stream to obtain the seventh stream containing propylene; and
(4-2) separating the seventh stream, and/or delivering at least a part of the seventh stream to the step (2) to obtain the C3 component stream.

* * * * *